(12) United States Patent
Hayashi et al.

(10) Patent No.: US 8,344,152 B2
(45) Date of Patent: *Jan. 1, 2013

(54) PROCESS FOR PRODUCING PYRIDYLETHYLTHIO COMPOUND, MODIFIED ION EXCHANGER AND PROCESS FOR PRODUCING THE SAME, AND PROCESS FOR PRODUCING BISPHENOL COMPOUND

(75) Inventors: Hideto Hayashi, Yokkaichi (JP); Koichi Hayashi, Kamisu (JP)

(73) Assignee: Mitsubishi Chemical Corporation, Tokyo (JP)

( * ) Notice: Subject to any disclaimer, the term of this patent is extended or adjusted under 35 U.S.C. 154(b) by 729 days.

This patent is subject to a terminal disclaimer.

(21) Appl. No.: 11/214,039

(22) Filed: Aug. 30, 2005

(65) Prior Publication Data

US 2006/0041145 A1 Feb. 23, 2006

Related U.S. Application Data

(63) Continuation of application No. PCT/JP2004/010467, filed on Jul. 23, 2004.

(30) Foreign Application Priority Data

Jul. 31, 2003 (JP) ................................. 2003-204361
Feb. 26, 2004 (JP) ................................. 2004-051424

(51) Int. Cl.
*C07D 213/00* (2006.01)

(52) U.S. Cl. ....................................................... 546/339

(58) Field of Classification Search .................... 546/339
See application file for complete search history.

(56) References Cited

U.S. PATENT DOCUMENTS

| 3,931,245 | A  | * | 1/1976  | Winter et al. ................. | 549/473 |
| 6,667,402 | B2 |   | 12/2003 | Sato et al.                    |         |
| 6,696,385 | B2 | * | 2/2004  | Hayashi et al. ............... | 502/216 |
| 6,720,426 | B2 | * | 4/2004  | Hayashi et al. ............... | 546/339 |
| 6,740,784 | B2 |   | 5/2004  | Iwahara et al.                 |         |
| 2003/0216578 | A1 |  | 11/2003 | Sato et al.                    |         |

FOREIGN PATENT DOCUMENTS

| DE | 1 0321677 | A1 | 12/2003 |
| JP | 53-144577 |    | 12/1978 |
| JP | 11-228540 |    | 8/1999  |
| JP | 11-228540 | A  | 8/1999  |
| JP | 11-255748 |    | 9/1999  |
| JP | 11-255748 | A  | 9/1999  |
| JP | 53-144577 | A  | 12/2001 |
| JP | 2001-335522 |  | 12/2001 |
| JP | 2001-335522 | A | 12/2001 |
| JP | 2002-003475 |  | 1/2002  |
| JP | 2002-220373 |  | 8/2002  |
| JP | 2002-220373 | A | 8/2002  |
| JP | 2002-220373 | * | 9/2002  |
| JP | 2003-12646 | A | 1/2003  |
| JP | 2004-161734 | A | 6/2004  |
| KR | 2003-0089449 | A | 11/2003 |
| KR | 2003089449 | A | 11/2003 |

OTHER PUBLICATIONS

International Search Report of PCT/JP2004/010467, mailed Nov. 2, 2004.
Bauer et al, "Addition of Thiourea to 2- and 4-Vinylpyridines," J. Org. Chem., Apr. 1961, vol. 26, No. 4, p. 82-85.
Database WPI Week 200234; Thomson Scientific, London, GB; AN 2002-298304; XP002506346.
Office Action in EP Application Serial No. 04 770 886.2 dated Apr. 20, 2011.
Bauer et al, "Addition of Thiourea to 2- and 4-Vinylpyridines", J. Org. Chem., vol. 26, 82-88 (1961).
English translation of Taiwanese Official Action dated Jul. 19, 2010 issued in Taiwanese application 93122439.

* cited by examiner

*Primary Examiner* — Janet Andres
*Assistant Examiner* — Heidi Reese
(74) *Attorney, Agent, or Firm* — Nixon & Vanderhye P.C.

(57) ABSTRACT

The present invention relates to a process for producing a pyridylethylthio compound which is improved in yield of the pyridylethylthio compound. In a process for producing a pyridylethylthio compound by reacting vinyl pyridine with a sulfur-containing compound, vinyl pyridine used contains a compound represented by the general formula (1):

(1)

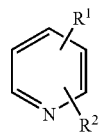

(wherein $R^1$ and $R^2$ are any of combination of isopropenyl group and a hydrogen atom, combination of 1-propenyl group and a hydrogen atom, combination of 2-propenyl group and a hydrogen atom, and combination of methyl group and vinyl group),
in an amount of not more than 4% by weight.

10 Claims, No Drawings

PROCESS FOR PRODUCING PYRIDYLETHYLTHIO COMPOUND, MODIFIED ION EXCHANGER AND PROCESS FOR PRODUCING THE SAME, AND PROCESS FOR PRODUCING BISPHENOL COMPOUND

This application is a Continuation of PCT/JP2004/010467, filed 23 Jul. 2004, claiming priority of Application Nos. JP 2003-204361, filed 31 Jul. 2003; and JP 2004-051424, filed 26 Feb. 2004. The entire contents of these applications are incorporated herein by reference.

TECHNICAL FIELD

The present invention relates to a process for producing a pyridylethylthio compound, a modified ion exchanger, a process for producing the ion exchanger, and a process for producing a bisphenol compound. The pyridylethylthio compound is useful not only as an intermediate product for synthesis of medicines, agricultural chemicals, etc., but also as a modifier for modifying a catalyst (acid ion exchanger) upon producing bisphenol A by condensation of phenol and acetone.

BACKGROUND ARTS

The synthesis of pyridylalkyl thiols has been conventionally described and reported in many documents and literatures. For example, in the case of synthesis of 2-(4-pyridyl)ethanethiol, there has been practically used the method of reacting 4-vinyl pyridine with thiourea in an ethanol solvent in the presence of p-toluenesulfonic acid to produce an isothiuronium salt, and then converting the thus obtained salt into 2-(4-pyridyl)ethanethiol in aqueous ammonia (for example, refer to "J. Org. Chem.", 26, 82(1961)). The above method has been continuously improved (for example, refer to Japanese Patent Application Laid-open (KOKAI) Nos. 11-228540 (1999) and 11-255748(1999)).

Also, there has been proposed the method of simply producing 2-(4-pyridyl)ethanethiol without isolating the isothiuronium salt by conducting a production reaction of the isothiuronium salt in an aqueous solvent, and then reacting the obtained reaction solution with aqueous ammonia solution (for example, refer to Japanese Patent Application Laid-open (KOKAI) No. 2002-220373).

As a method for producing 4-vinyl pyridine as one of the starting materials of the above 2-(4-pyridyl)ethanethiol, there is generally known the method of subjecting γ-picoline and formaldehyde to methylolation reaction to produce 2-(4-pyridyl)ethanol, and then subjecting the thus produced 2-(4-pyridyl)ethanol to dehydration reaction (for example, refer to Japanese Patent Application Laid-open (KOKAI) No. 53-144577(1978)). The thus produced 4-vinyl pyridine contains several kinds of impurities even after being purified, for example, by distillation. These impurities include γ-picoline as an unreacted raw material, as well as various by-products such as ethyl pyridine, isopropenyl pyridine, propenyl pyridine and methylvinyl pyridines having methyl and vinyl groups bonded to a pyridine skeleton thereof.

In addition to the above methods, there are also known the following methods. That is, there have been proposed the method of using as a sulfur-containing compound, a thioacetic acid instead of urea, and reacting the thioacetic acid with vinyl pyridine to produce pyridylethylthioacetate as a pyridylethylthio compound (for example, refer to U.S. Pat. Nos. 6,534,686 and 6,620,939), and the method of reacting vinyl pyridine with hydrogen sulfide as the sulfur-containing compound to produce pyridylethanethiol as the pyridylethylthio compound (for example, refer to U.S. Pat. No. 6,667,402). Meanwhile, the above pyridylethylthioacetate is decomposed in the presence of an acid and readily converted into pyridylethanethiol. However, the pyridylethylthioacetate as a pyridylethanethiol derivative having a mercapto group protected by an acetyl group may also be directly as a modifier for modifying a catalyst used upon producing bisphenol A by condensation of phenol and acetone.

DISCLOSURE OF THE INVENTION

Problem to be Solved by the Invention

However, when the vinyl pyridine is reacted with the sulfur-containing compound according to the above conventional methods, there arises such a problem that a yield of the pyridylethylthio compound is unexpectedly lowered.

Meanwhile, in the conventionally proposed methods, there have been studied pretreatments of vinyl pyridine, specifically 4-vinyl pyridine, such as simple distillation for the purpose of removal of coloring substances and polymers thereof. However, no studies have been presently made from the standpoint of yield of pyridylethylthio compounds.

In addition, in the production of bisphenol A, as an acid catalyst, there has been used a modified ion exchanger of which acid group is at least partially protected with a pyridylethylthio compound which is obtained by reacting an acid ion exchanger with a modifier composed of a mercaptoalkylpyridine compound or its derivative having a protected mercapto group. The above modifier has a function as an accelerator for enhancing an activity of the catalyst. As a method of producing such a modified ion exchanger, there are known the following methods.

(1) The method of charging an acid ion exchanger in a batch-type reactor, and then charging an aqueous solution in which the modifier is dissolved, an aqueous acid solution and a phenol solution thereinto (for example, Japanese Patent Application Laid-open (KOKAI) Nos. 9-24279(1997), 2001-335522 and 2003-246760, Japanese Patent Publication (KOKOKU) No. 63-14690(1988) and U.S. Pat. No. 6,534,686); and (2) the method of flowing an aqueous acid solution or a phenol solution in which the modifier is dissolved, through a reactor previously filled with an acid ion exchanger (for example, Japanese Patent Application Laid-open (KOKAI) No. 8-40961(1996)).

Meanwhile, a large amount of bisphenol A has been consumed as a raw material, for example, upon production of epoxy resins, polycarbonate resins, phenol resins or polyester resins. Therefore, bisphenol A has now been produced in an amount as large as, for example, not less than 20,000 tons per year in an industrial scale. Accordingly, in the production of bisphenol A, it is industrially important to enhance a performance of the catalyst used therein even to a small extent, for example, to enhance a conversion rate or selectivity to the aimed product even by 1%.

The present invention has been performed in view of the above problems. An object of the present invention is to provide a process for producing a pyridylethylthio compound which is improved in yield thereof.

Another object of the present invention is to provide a modified ion exchanger produced using the pyridylethylthio compound produced by the above process as a modifier.

A further object of the present invention is to provide a process for producing the modified ion exchanger which can be used as a catalyst having a more excellent performance upon production of bisphenol compounds.

A still further object of the present invention is to provide a process for producing a bisphenol compound using the above modified ion exchanger as a catalyst.

Means for Solving Problems

As a result of the present inventors' earnest studies, it has been found that when concentrations of specific impurities contained in raw vinyl pyridine are respectively limited to not more than a predetermined value, the yield of the pyridylethylthio compound can be improved. Also, it has been found that when the reaction between an acid ion exchanger and a modifier is conducted by the quite different method from the conventional methods, there can be obtained a modified ion exchanger which serves as a catalyst having a more excellent performance upon production of bisphenol compounds. The present invention has been attained based on the above findings. The present invention includes a plurality of aspects as described below which are associated with each other.

In a first aspect of the present invention, there is provided a process for producing a pyridylethylthio compound by reacting vinyl pyridine with a sulfur-containing compound, wherein the said vinyl pyridine used contains a compound represented by the general formula (1):

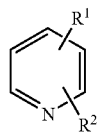

(1)

(wherein $R^1$ and $R^2$ are any of combination of isopropenyl group and a hydrogen atom, combination of 1-propenyl group and a hydrogen atom, combination of 2-propenyl group and a hydrogen atom, and combination of methyl group and vinyl group),
in an amount of not more than 4% by weight.

In a second aspect of the present invention, there is provided a modified ion exchanger comprising an acid ion exchanger of which acid group is at least partially protected with a pyridylethylthio compound, wherein a mercaptoalkylpyridine compound produced by the process as defined above or a derivative thereof having a protected mercapto group is used as a modifier for the acid ion exchanger.

In a third aspect of the present invention, there is provided a process for producing a bisphenol compound, comprising reacting a phenol compound with a carbonyl compound in the presence of the modified ion exchanger as defined above.

In a fourth aspect of the present invention, there is provided a process for producing a modified ion exchanger comprising an acid ion exchanger of which acid group is at least partially protected with a pyridylethylthio compound by reacting the acid ion exchanger with a modifier composed of a mercaptoalkylpyridine compound or a derivative thereof having a protected mercapto group, wherein the modifier dispersed in a dispersion medium is contacted with the acid ion exchanger to modify at least a part of the acid group of the acid ion exchanger.

In a fifth aspect of the present invention, there is provided a process for producing a bisphenol compound, comprising reacting a phenol compound with a carbonyl compound in the presence of the modified ion exchanger produced by the process as defined above.

Effect of the Invention

According to the present invention, there are provided a process for producing a pyridylethylthio compound, which process is improved in yield of the aimed compound; a modified ion exchanger which is useful as an acid catalyst upon producing bisphenol compounds by condensation of a phenol compound and a carbonyl compound; and an industrially useful process for producing bisphenol compounds.

PREFERRED EMBODIMENT OF THE INVENTION

The present invention is described in detail below.

First, the process for producing a pyridylethylthio compound according to the present invention is explained. The vinyl pyridine used as a raw material of the pyridylethylthio compound includes position isomers which are different in position of the vinyl group bonded to pyridine ring from each other. In the present invention, any of these isomers, for example, 2-vinyl pyridine and 4-vinyl pyridine, may be suitably used. Of these isomers, preferred is 4-vinyl pyridine. The kinds of sulfur-containing compounds used as the other raw material are not particularly restricted, and any suitable sulfur-containing compounds may be used as long as the compounds are capable of producing the aimed pyridylethylthio compound by reacting with vinyl pyridine. Specific examples of the sulfur-containing compounds may include thiourea, thioacetic acid, hydrogen sulfide, sodium sulfide, sodium thiosulfate and thiol compounds. Of these sulfur-containing compounds, preferred are thiourea, thioacetic acid and hydrogen sulfide, and more preferred are thiourea and thioacetic acid.

As described in the prior arts, the pyridylethylthio compounds produced are varied depending upon kinds of the raw sulfur-containing compounds used. Examples of the pyridylethylthio compounds according to the present invention may include isothiuronium ethyl pyridinium salts, pyridylethanethiol, pyridylethanethiol derivatives having a protected mercapto group such as pyridylethylthioacetate, and alkyl (pyridylethyl)sulfides. An example of respective reactions using thiourea, thioacetic acid or hydrogen sulfide as the raw sulfur-containing compound is described below.

The reaction using thiourea as the sulfur-containing compound is as follows. That is, vinyl pyridine is reacted with thiourea in the presence of an acid to obtain an isothiuronium salt represented by the following general formula (2) as the pyridylethylthio compound.

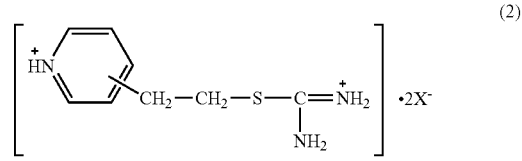

(2)

The above isothiuronium salt is decomposed in the presence of an alkali, and converted into pyridylethanethiol represented by the following general formula (3) as the pyridylethylthio compound.

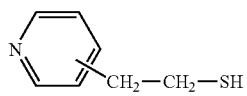
(3)

The reaction using thioacetic acid as the sulfur-containing compound is as follows. That is, vinyl pyridine is reacted with thioacetic acid to obtain pyridylethylthioacetate represented by the following general formula (4) as the pyridylethylthio compound.

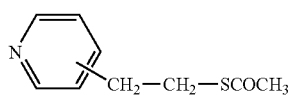
(4)

The above pyridylethylthioacetate is decomposed in the presence of an acid, and converted into pyridylethanethiol represented by the above general formula (3) as the pyridylethylthio compound.

The reaction using hydrogen sulfide as the sulfur-containing compound is as follows. That is, vinyl pyridine is reacted with hydrogen sulfide to obtain pyridylethanethiol represented by the above general formula (3) as the pyridylethylthio compound.

Any of the above reactions are already described in the prior arts. In the present invention, the reaction conditions described in the prior arts may be directly applied to these reactions. In the reaction using thiourea as the sulfur-containing compound, preferred reaction conditions are as follows.

As the acid, there may be suitably used organic acids such as p-toluenesulfonic acid, benzenesulfonic acid and trifluoromethanesulfonic acid, as well as ordinary inorganic acids such as sulfuric acid, hydrochloric acid and nitric acid. Of these acids, from the standpoint of good handling property, preferred are aromatic sulfonic acids such as p-toluenesulfonic acid and benzenesulfonic acid, and sulfuric acid, and more preferred are p-toluenesulfonic acid and sulfuric acid.

The acid may be used in a stoichiometric amount or more relative to vinyl pyridine as shown in the above formulae. However, when the acid is used in a too excess amount relative to vinyl pyridine, undesirable side reactions tend to be caused. Therefore, the acid is used in an amount of usually not more than 4 equivalents, preferably not more than 3 equivalents based on one equivalent of vinyl pyridine. Also, thiourea may be used in a stoichiometric amount or slightly excess amount, specifically in an amount of usually not more than 1.5 equivalents, preferably not more than 1.3 equivalents based on one equivalent of vinyl pyridine.

The reaction for production of the pyridylethylthio compound may be conducted by adding the acid and thiourea to an organic solvent such as alcohols or an aqueous solvent to dissolve these compounds in the solvent, and then dropping vinyl pyridine into the obtained solution under stirring. The reaction is preferably conducted in an inert gas atmosphere such as nitrogen. The concentration of the acid is preferably as high as possible unless an easiness of the reaction procedure is adversely influenced. For example, the concentration of p-toluenesulfonic acid is usually 5 to 50% by weight, preferably 20 to 40% by weight. The reaction temperature is usually 30 to 100° C., preferably 50 to 100° C., and the reaction time is usually 1 to 10 hours.

Then, in the present invention, after completion of the production reaction of the isothiuronium salt, the resultant isothiuronium salt is decomposed in the presence of an alkali to produce pyridylethanethiol. More specifically, alkali is added to the above-obtained reaction solution to adjust a liquid nature of the reaction solution to alkaline. The preferred alkali used is ammonia though metal hydroxides such as sodium hydroxide may also be used as the alkali. When ammonia is used as the alkali, the decomposition reaction proceeds as follows.

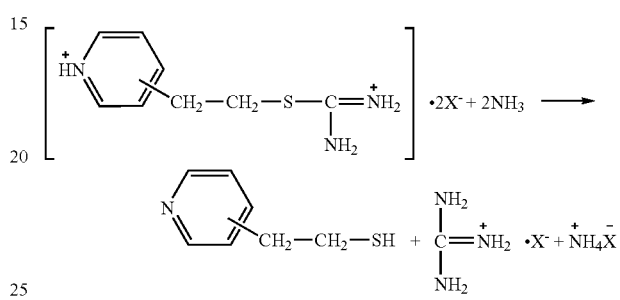

The necessary amount of ammonia used in the above reaction is stoichiometrically 2 moles per mole of the isothiuronium salt. However, ammonia is practically used in an excess amount relative to the isothiuronium salt so as to allow the reaction to proceed sufficiently. More specifically, the amount of ammonia used is a sum of the amount required for neutralizing an acid contained in the isothiuronium salt solution obtained in the previous step and the above-mentioned amount. That is, the amount of ammonia used is usually 3 to 15 moles, preferably 3 to 5 moles per mole of the raw vinyl pyridine. When the amount of ammonia used is too large, the yield of the aimed compound generally tends to be deteriorated. The reason therefor is suggested such that pyridylethanethiol as produced undergoes undesirable side reactions. Meanwhile, ammonia is usually used in the form of aqueous ammonia because of easy handing thereof. The concentration of ammonia in the aqueous ammonia may be appropriately determined in consideration of good operability of subsequent filtration and extraction steps.

The conversion reaction of the isothiuronium salt into pyridylethanethiol may be conducted under stirring at a temperature of 30 to 70° C. for 0.5 to 10 hours. Although the conversion reaction may proceed at room temperature, the reaction rate tends to become low. On the other hand, when the conversion reaction is conducted under a high-temperature condition, undesirable side reactions tend to be caused, resulting in deterioration in yield of the aimed compound.

After completion of the conversion reaction, when an aromatic sulfonic acid is used as the acid, the reaction solution is cooled to about 10° C. to precipitate by-produced guanidinium salts. Then, an extraction solvent such as toluene is added to the reaction solution, and the resultant solution is filtered to remove impurities therefrom. The obtained filter cake is further washed with the extraction solvent, and the washing liquid is mixed with the filtrate. The mixed filtrate is separated into respective liquid phases to recover an extraction solvent phase therefrom.

On the other hand, in the case where an inorganic acid such as sulfuric acid is used as the acid, the guanidinium salts are not precipitated even when the reaction solution is cooled.

Therefore, the filtration procedure may be omitted, and the reaction solution may be directly subjected to the extraction procedure using an organic solvent. Also, a small amount of polymeric insoluble substances may be contained in the reaction solution depending upon the reaction conditions. In such cases, a small amount of an acid may be added to the reaction solution to adjust a liquid nature of the reaction solution to neutral. As a result, since the insoluble substances can be dissipated, the reaction solution may be directly subjected to the extraction procedure.

In any of the above cases, the resultant aqueous phase is further extracted with the extraction solvent, and the resultant extraction solvent phase is mixed with the previously obtained extraction solvent phase. Then, after the mixed extraction solvent phase is distilled to remove the extraction solvent therefrom, the obtained residual liquid is subjected to distillation under reduced pressure, thereby obtaining the aimed pyridylethanethiol.

The important feature of the present invention lies in that in the process for producing a pyridylethylthio compound by reacting vinyl pyridine with a sulfur-containing compound, an amount of a compound which is contained in the vinyl pyridine used and which is represented by the general formula (1):

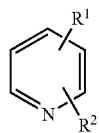

(1)

(wherein $R^1$ and $R^2$ are any of combination of isopropenyl group and a hydrogen atom, combination of 1-propenyl group and a hydrogen atom, combination of 2-propenyl group and a hydrogen atom, and combination of methyl group and vinyl group),
is usually not more than 4% by weight.

As described above, in general, vinyl pyridine may be produced by subjecting picoline and formaldehyde to methylolation reaction to produce pyridyl ethanol, and then subjecting the thus obtained pyridyl ethanol to dehydration reaction in the presence of an alkali. Upon production of 4-vinyl pyridine, γ-picoline and formaldehyde are subjected to methylolation reaction to produce 2-(4-pyridyl)ethanol. These vinyl pyridine products tend to contain as impurities, unreacted γ-picoline as well as ethyl pyridine and various by-produced compounds represented by the above general formula (1), specifically isopropenyl pyridine ($R^1$ and $R^2$ are $C(CH_3)=CH_2$ and H, respectively), 1-propenyl pyridine ($R^1$ and $R^2$ are $CH=CH-CH_3$ and H, respectively), 2-propenyl pyridine ($R^1$ and $R^2$ are $CH_2-CH=CH_2$ and H, respectively), and methylvinyl pyridine ($R^1$ and $R^2$ are $CH_3$ and $CH=CH_2$, respectively).

According to the present inventors' knowledge, in the process for production of various pyridylethylthio compounds such as 2-(4-pyridyl)ethanethiol, γ-picoline or ethyl pyridine is not concerned in the production reaction and, therefore, remain unreacted even after completion of the reaction. Whereas, the compounds represented by the above general formula (1) have substantially no contribution to the reaction between vinyl pyridine and the sulfur-containing compound and, therefore, remain unreacted. However, the compounds tend to be reacted with the produced pyridylethylthio compound to form sulfides, resulting in deteriorated recovery rate of the pyridylethylthio compound. Of the compounds represented by the above general formula (1), isopropenyl pyridine has especially large adverse influences on the recovery rate of the aimed compound.

The method of controlling the content of the compounds represented by the general formula (1) in the raw vinyl pyridine to not more than 4% by weight is not particularly restricted, and there may be usually used purification methods using a distillation procedure. For example, vinyl pyridine is purified using a pressure-reducing distillation facility equipped with a packed column. More specifically, the purification methods may be conducted using a packed column having usually not less than 2 stages, preferably 3 to 10 stages, while controlling reaction conditions therein such as reaction pressure such that the temperature at a top of the column is in the range of 80 to 150° C.

The pyridylethylthio compound as the reaction product preferably contains the compounds represented by the general formula (1) in an amount of not more than 3% by weight. The content of the compounds represented by the general formula (1) in the pyridylethylthio compound is preferably as low as possible. However, in order to achieve an extremely low content of the compounds, costs required for the distillation procedure tend to be too high, resulting in loss of the raw materials. Therefore, the lower limit of the content of the compounds represented by the general formula (1) is usually 0.1% by weight.

Next, the modified ion exchanger of the present invention is explained. The modified ion exchanger of the present invention is constituted of an acid ion exchanger of which acid group is at least partially protected by the pyridylethylthio compound. In the present invention, as the modifier for modifying the acid ion exchanger, there is used a mercaptoalkylpyridine compound produced by the above process for production of the pyridylethylthio compound or its derivative having a protected mercapto group.

As the acid ion exchanger, those ion exchangers that are conventionally known as an acid catalyst for production of bisphenol A may be used without limitations. The acid ion exchanger may be usually made of sulfonic acid-type ion exchange resins. Examples of base resins used in the acid ion exchanger may include styrene-divinylbenzene copolymers, perfluoroethylene copolymers, and phenol-formaldehyde polymers. Among these resins, styrene-divinylbenzene copolymers may be usually used. Examples of the materials other than resins may include sulfonic acid group-containing polysiloxanes described, for example, in Japanese Patent Application Laid-open (KOKAI) No. 2003-24670, and sulfonic acid group-containing mesoporous silica.

Whereas, examples of the mercaptoalkylpyridine compounds used as the modifier may include mercaptomethyl pyridine, mercaptoethyl pyridine or the like. Examples of the derivatives having a protected mercapto group may include pyridylalkylthioacetates. Of these modifiers, especially preferred is 2-(4-pyridyl)ethanethiol.

In the present invention, the above acid ion exchanger is reacted with the modifier to produce the modified ion exchanger of which acid group is at least partially protected with the pyridylethylthio compound. The amount of the modifier used is usually 2 to 30 mol %, preferably 5 to 20 mol % based on the acid group (sulfonic acid group) of the acid ion exchanger. When the reaction is conducted under the above reaction conditions, it becomes possible to produce the modified ion exchanger of which acid group is partially neutralized. The other reaction conditions may be the same as known conditions described in the prior arts. Meanwhile, the modifier, for example, pyridylethylthio acetate, may be directly used without deprotecting or deblocking the acid group. However, some modifiers are required to undergo deprotecting or deblocking before use depending upon kinds of protected acid groups. An example of the modifiers requiring the deprotecting or deblocking procedure before use is t-butyl sulfide.

Next, the process for producing the modified ion exchanger is explained. The present invention further lies in that in the process for producing the modified ion exchanger of which acid group is at least partially protected with the pyridylethylthio compound by reacting the acid ion exchanger with the modifier composed of a mercaptoalkylpyridine compound or its derivative having a protected mercapto group, the modifier dispersed in a dispersion medium is contacted with the acid ion exchanger to modify at least a part of the acid group of the acid ion exchanger.

As the acid ion exchanger as well as the mercaptoalkylpyridine compound or its derivative having a protected mercapto group, there may be used the same materials and compounds as described above. In particular, the preferred modifiers are those compounds produced according to the process for producing the pyridylethylthio compound. The amount of the modifier used is also the same as described above.

Thus, the feature of the present invention lies in that the modifier dispersed in a dispersion medium is contacted with the acid ion exchanger to modify at least a part of the acid group of the acid ion exchanger. As the dispersion medium, there may be usually used water. All of the above modifiers have a hetero ring and, therefore, are compounds having a low solubility in water. Therefore, the above modifiers are readily emulsified in water by stirring therein. In the obtained emulsion, the modifier is present in a liquid phase in the form of fine oil droplets. Usually, when the stirring is stopped, the oil droplets are agglomerated together to form an oil phase, thereby separating the liquid phase into two layers.

The amount of water used for emulsifying the modifier is not particularly restricted. For example, the weight ratio of water to the modifier is in the range of usually 5 to 300, preferably 6 to 200 in consideration of good contact with the acid ion exchanger. The temperature used upon the modification reaction is not particularly restricted as long as the modifier is well emulsified in water. Usually, a room temperature is sufficiently usable as the modification reaction temperature. The modification reaction time is usually 0.2 to 5 hours.

When the modification reaction is initiated by contacting the acid ion exchanger with the modifier in the form of an emulsion, the modifier is continuously consumed as the reaction proceeds, so that the emulsion condition is gradually dissipated.

In the conventional methods, modifiers which are hardly soluble in water have been dissolved, for example, in an aqueous acid solution, and used in the form of a uniform solution. In the case of using the modified ion exchanger produced according to the process of the present invention, the conversion rate of acetone upon production of bisphenol A can be enhanced as compared to the use of the conventional modified ion exchanger having the same modification percentage. The reason therefor is considered, though not necessarily clear, to be that the modifier in the form of an emulsion exhibits a high reactivity to the acid group present on the surface of the acid ion exchanger, so that the obtained modified ion exchanger has a slightly higher modification percentage on the surface of the acid ion exchanger than an average modification percentage of the acid ion exchanger as a whole, thereby enhancing the conversion rate of acetone.

Examples of a method of conducting the emulsification of the modifier and the modification reaction of the acid ion exchanger at the same time, may include (1) the method of charging water and the acid ion exchanger into a closed-system reaction vessel, and then adding the modifier into the reaction vessel under stirring so as to applying a sufficient power for dispersing the acid ion exchanger in the liquid; and (2) the method of charging the modifier through a feed port of a transportation line through which a water slurry of the acid ion exchanger is transported to a container or a reactor using an ejector or a slurry pump.

Although the dispersion medium used for forming the emulsion of the modifier is not limited to water, the use of water as the dispersion medium is more advantageous because post-treatments of the reaction solution obtained after the modification reaction become more facilitated. Also, in the process for producing the modified ion exchanger according to the present invention, since the modifier in the form of an emulsion is subjected to the modification reaction, there can be obtained various advantages such as, for example, low costs of chemicals used, low costs for post-treatments after the modification reaction, and no corrosion problems by chemicals, as compared to the conventional methods requiring the use of an aqueous acid solution for dissolving the modifier therein.

Next, the process for producing a bisphenol compound according to the present invention is explained. The production process lies in the reaction of a phenol compound with a carbonyl compound in the presence of the above modified ion exchanger.

In a typical example of the above production process of the present invention, phenol as the phenol compound is reacted with acetone as the carbonyl compound to produce bisphenol A. However, the production process of the present invention is not limited to the process for production of bisphenol A, and various phenol compounds may be reacted with various aliphatic or aromatic ketones or aldehydes to produce various phenol compounds. These production processes may be conducted under conventionally known conditions except using the above modified ion exchanger according to the present invention as the catalyst. More specifically, bisphenol A is produced by reacting phenol with acetone to obtain bisphenol A, recovering a phenol solution containing the thus obtained bisphenol A from the resultant reaction solution, cooling the thus recovered phenol solution containing bisphenol A to obtain crystallized adducts composed of bisphenol A and phenol, and then removing-phenol from the crystallized adducts.

EXAMPLES

The present invention is described in more detail below by the following examples. However, these examples are only illustrative and not intended to limit the scope of the present invention.

Example 1

A 200 mL round bottom flask was charged with 102 g of a 30 wt % sulfuric acid aqueous solution and 11.4 g of thiourea, and then an inside of the reactor was purged with nitrogen. Thereafter, the contents of the flask were heated to 70° C. under stirring. 15.8 g of 4-vinyl pyridine containing 0.2% by weight of isopropenyl pyridine as impurity and having a purity of 98.6% (net of 4-vinyl pyridine: 15.5 g; 148.5 mmol) was dropped into the obtained reaction solution over one hour. After completion of the dropping, the reaction solution was further reacted for 5 hours. One gram of the resultant reaction solution was sampled and mixed with 4 g of toluene and 0.5 g of a 10% ammonia aqueous solution, and then the resultant mixture was stirred. A toluene phase was separated from the obtained reaction mixture and subjected to quantitative analysis. As a result, it was confirmed that the conversion rate of 4-vinyl pyridine was 99.9%, and substantially no residual isopropenyl pyridine was present.

After completion of the reaction, the obtained reaction solution was cooled to 20° C., and 45.6 g of a 28% ammonia aqueous solution was added thereto over 2 hours. Thereafter, the reaction solution was heated to 40° C. and reacted for 3 hours. After completion of the reaction, the obtained reaction solution was cooled to 20° C., and then extracted with toluene three times. As a result of analyzing the thus recovered toluene phase by gas chromatography, it was confirmed that 17.6 g of 2-(4-pyridyl)ethanethiol was produced, and the yield thereof was 85.1% when calculated on the basis of the net of 4-vinyl pyridine.

Example 2

The same procedure as defined in Example 1 was conducted except that 15.8 g of 4-vinyl pyridine having a purity of 96.0% and containing 1.9% by weight of isopropenyl pyridine (net of 4-vinyl pyridine: 15.2 g; 144.0 mmol) was used. As a result of analyzing the reaction solution before dropping ammonia thereto, it was confirmed that the conversion rate of 4-vinyl pyridine was 99.9% when calculated on the basis of the net of 4-vinyl pyridine, and residual isopropenyl pyridine was present in an amount of 0.9 mmol. Further, after completion of the decomposition reaction conducted by adding ammonia, the reaction solution was extracted with toluene. As a result of analyzing the recovered toluene phase by gas chromatography, it was confirmed that 16.2 g of 2-(4-pyridyl)ethanethiol was produced (yield: 83.8% when calculated on the basis of the net of 4-vinyl pyridine).

Comparative Example 1

The same procedure as defined in Example 1 was conducted except that 15.8 g of 4-vinyl pyridine having a purity of 94.0% and containing 4.5% by weight (6.0 mmol) of isopropenyl pyridine (net of 4-vinyl pyridine: 14.8 g; 141.0 mmol) was used. As a result of analyzing the reaction solution before dropping ammonia thereto, it was confirmed that the conversion rate of 4-vinyl pyridine was 99.7%, and residual isopropenyl pyridine was present in an amount of 1.3 mmol. Further, after completion of the decomposition reaction conducted by adding ammonia, the reaction solution was extracted with toluene. As a result of analyzing the recovered toluene phase by gas chromatography, it was confirmed that 15.9 g of 2-(4-pyridyl)ethanethiol was produced (yield: 80.9% when calculated on the basis of the net of 4-vinyl pyridine).

Example 3

15.2 g of thioacetic acid was charged into a 100 mL three-necked flask under a nitrogen atmosphere, and cooled by ice water. After cooling the liquid temperature within the flask to 5° C., 21.0 g of 4-vinyl pyridine containing 1.1% by weight of 4-isopropyl pyridine was dropped into the flask over one hour. The liquid temperature within the flask was gradually raised, and reached 11° C. upon completion of the dropping. After completion of the dropping, the reaction was further continued under stirring. After one hour, the reaction solution was analyzed by gas chromatography. As a result, it was confirmed that the conversion rate of 4-vinyl pyridine was 94.7%; 33.5 g of 4-pyridylethylthioacetate as a main product (96.3% by weight based on the reaction product) was produced; and 2-methyl-2-(4-pyridyl)ethyl thioacetate as an addition reaction product of 4-isopropenyl pyridine with thioacetic acid was produced in an amount of 0.9% by weight based on the reaction product.

Comparative Example 2

The same procedure as defined in Example 3 was conducted except that 7.6 g of thioacetic acid and 10.5 g of 4-vinyl pyridine containing 4.6% by weight of 4-isopropenyl pyridine were charged. As a result, it was confirmed that the conversion rate of 4-vinyl pyridine was 94.0%; 32.1 g of 4-pyridylethylthioacetate (92.7% by weight based on the reaction product) was produced; and 2-methyl-2-(4-pyridyl)ethylthioacetate was produced in an amount of 4.4% by weight based on the reaction product.

Example 4

40 g of a wetted strong acid ion exchange resin "DIAION SK104H" (acid exchange capacity: 1.67 mmol/g under wetted condition; DIAION is registered trademark owned by Mitsubishi Chemical Corp.) and 80 g of distilled water were charged into a 200 mL of four-necked flask and stirred at room temperature to wash the ion exchange resin. The washing liquid was removed by decantation, and distilled water was added again to the resin. This washing procedure was repeated five times.

Then, after removing the washing liquid, 80 g of distilled water (pH: 6.1) was added to the resin, and then an inside of the flask was purged with nitrogen. Then, 1.46 g (10.5 mmol) of 2-(4-pyridyl)ethanethiol was added into the flask under stirring at one time, and the contents of the flask were further stirred at a rotating speed of 250 rpm for 3 hours to conduct a modification reaction of the resin. As a result, it was confirmed that although at an initial stage of the reaction, the reaction solution was slightly turbid owing to suspended 2-(4-pyridyl)ethanethiol, the turbidity of the reaction solution was gradually reduced with the passage of time, and after the elapse of about one hour, almost the whole turbidity was dissipated. Further, when the reaction was continued, the reaction solution showed no turbidity upon completion of the reaction.

After completion of the reaction, the reaction solution was decanted to remove a liquid therefrom. The liquid removed by decantation had a pH value of 5.0. Then, 80 g of distilled water was added to the ion exchange resin remaining in the flask, and stirred for 30 min, followed by subjecting the resultant mixture to decantation to remove a liquid therefrom. After the above catalyst washing procedure was repeated five times, the contents of the flask were filtered to remove a liquid therefrom and recover the ion exchange resin. As a result of measurement of residual mercapto and sulfonic acid groups in the thus recovered ion exchange resin, it was confirmed that the modification percentage of the ion exchange resin was 14.7%, and the residual sulfonic acid percentage was 84.4%.

Next, 7.5 mL of the above catalyst was filled in a glass tube having an inner diameter of 12 mm, and water contained in the catalyst was replaced with phenol. Then, a phenol solution containing 4.5% by weight of acetone was flowed through the catalyst at a feed rate of 26.3 mL/h, and reacted at a catalyst layer temperature of 70° C. After the elapse of 6 hours from initiation of flowing the phenol solution, the reaction solution was sampled at an outlet of the reaction tube, and analyzed by gas chromatography. As a result, it was confirmed that the concentration of acetone in the reaction solution was 0.71% by weight (acetone conversion rate: 84.3%), and the concentration of p,p-BPA produced was 14.1%.

Example 5

40 g of a wetted strong acid ion exchange resin "DIAION SK104H" (acid exchange capacity: 1.67 mmol/g under wetted condition) and 100 g of distilled water were charged into a 200 mL of four-necked flask and stirred at 60° C. to wash the ion exchange resin. The washing liquid was removed by decantation, and distilled water was introduced again to the flask. This washing procedure was repeated five times.

Then, after removing the washing liquid, 40 g of distilled water (pH: 6.1) was added to the resin, and then an inside of the flask was purged with nitrogen. Then, 1.95 g (10.8 mmol) of 4-pyridylethylthioacetate was added into the flask, and the contents of the flask were stirred at a rotating speed of 250 rpm for 3 hours. As a result, it was confirmed that although at an initial stage of the reaction, the reaction solution was slightly turbid in yellow color owing to suspended 4-pyridylethylthioacetate, the reaction solution showed no turbidity upon completion of the reaction. After completion of the reaction, the reaction solution was decanted to remove a liquid therefrom. The liquid removed by decantation had a pH value of 2.9. Then, 100 g of distilled water was added to the ion exchange resin remaining in the flask, and stirred for 30 min, followed by subjecting the resultant mixture to decantation to remove a liquid therefrom. After the above catalyst washing procedure was repeated five times, the contents of the flask were filtered to remove a liquid therefrom and recover the ion exchange resin. As a result of measurements of residual mercapto and sulfonic acid groups in the thus recovered ion exchange resin, it was confirmed that the modification percentage of the ion exchange resin was 15.2%, and the residual sulfonic acid percentage was 84.6%.

Next, 7.5 mL of the above catalyst was sampled, and subjected to the reaction under the same conditions as defined in Example 4. After 6 hours, the reaction solution was sampled at an outlet of the reaction tube. As a result of analyzing the thus sampled reaction solution, it was confirmed that the concentration of acetone in the reaction solution was 0.73% by weight (acetone conversion rate: 83.9%), and the concentration of p,p-BPA produced was 14.6% by weight.

Comparative Example 3

The same procedure as defined in Example 4 was conducted except that after washing the ion exchange resin with distilled water, 80 g of an aqueous sulfuric acid solution having a pH value of 1.2 was added instead of 80 g of distilled water (pH: 6.1), thereby preparing the catalyst. In this case, 2-(4-pyridyl)ethanethiol was immediately dissolved and, therefore, formed no emulsion. The reaction solution was subjected to decantation to remove a liquid therefrom. After repeating the above washing procedure, thee ion exchange resin was recovered. As a result of measurements of residual mercapto and sulfonic acid groups in the thus recovered ion exchange resin, it was confirmed that the modification percentage of the ion exchange resin was 15.2%, and the residual sulfonic acid percentage was 84.7%.

Next, 7.5 mL of the above catalyst was sampled, and subjected to the reaction under the same conditions as defined in Example 4. After 6 hours, the reaction solution was sampled at an outlet of the reaction tube. As a result of analyzing the thus sampled reaction solution, it was confirmed that the concentration of acetone in the reaction solution was 0.79% by weight (acetone conversion rate: 82.7%), and the concentration of p,p-BPA produced was 13.4% by weight.

The invention claimed is:

1. A process for producing pyridylethanethiol by a process comprising a first process as defined in step (1):
    (1) producing vinylpyridine by subjecting picoline and formaldehyde to methylolation reaction to produce pyridyl ethanol, and then subjecting the pyridyl ethanol to a dehydration reaction in the presence of an alkali;
    and a second step selected from any one of the following steps (2) to (4):
    (2) reacting vinylpyridine with thiourea as a sulfur-containing compound in the presence of an acid to obtain an isothiuronium salt, and decomposing said isothiuronium salt in the presence of an alkali to convert it into pyridylethanethiol;
    (3) reacting vinylpyridine with thioacetic acid as a sulfur-containing compound to obtain pyridylethyl thioacetate, and decomposing said pyridylethyl thioacetate in the presence of an acid to convert it into pyridylethanethiol; and
    (4) reacting vinyl pyridine with hydrogen sulfide as a sulfur-containing compound to obtain pyridylethanethiol,
    wherein in the process said vinyl pyridine comprises, as an impurity, isopropenyl pyridine, and
    wherein in the process isopropenyl pyridine as the impurity is removed by distillation of said vinyl pyridine so that a content of isopropenyl pyridine in said vinyl pyridine is not more than 4% by weight.

2. The process according to claim 1, wherein the distillation of said vinyl pyridine is conducted using a pressure-reducing distillation facility equipped with a packed column.

3. The process according to claim 1, wherein the distillation of said vinyl pyridine is conducted using a packed column having not less than 2 stages.

4. The process according to claim 1, wherein the distillation of said vinyl pyridine is conducted using a packed column having 3 to 10 stages.

5. The process according to claim 1, wherein the distillation of said vinyl pyridine is conducted under conditions such that the temperature at a top of the distillation column is in a range of 80 to 150° C.

6. A process for producing pyridylethyl thioacetate by a process comprising a first process as defined in step (1):
    (1) producing vinylpyridine by subjecting picoline and formaldehyde to methylolation reaction to produce pyridyl ethanol, and then subjecting the pyridyl ethanol to a dehydration reaction in the presence of an alkali;
    and a second step of
    (2) reacting vinylpyridine with thioacetic acid as a sulfur-containing compound to convert it into pyridylethyl thioacetate;
    wherein in the process said vinyl pyridine comprises, as an impurity, isopropenyl pyridine, and
    wherein in the process isopropenyl pyridine as the impurity is removed by distillation of said vinyl pyridine so that a content of isopropenyl pyridine in said vinyl pyridine is not more than 4% by weight.

7. The process according to claim 6, wherein the distillation of said vinyl pyridine is conducted using a pressure-reducing distillation facility equipped with a packed column.

8. The process according to claim 6, wherein the distillation of said vinyl pyridine is conducted using a packed column having not less than 2 stages.

9. The process according to claim 6, wherein the distillation of said vinyl pyridine is conducted using a packed column having 3 to 10 stages.

10. The process according to claim 6, wherein the distillation of said vinyl pyridine is conducted under conditions such that the temperature at a top of the distillation column is in a range of 80 to 150° C.

* * * * *